(12) United States Patent
Wiegel et al.

(10) Patent No.: US 12,295,797 B2
(45) Date of Patent: May 13, 2025

(54) SYSTEMS, METHODS, AND DEVICES FOR PROVIDING AN AUGMENTED DISPLAY

(71) Applicant: Medtronic Navigation, Inc., Louisville, CO (US)

(72) Inventors: Stephanie Elizabeth Wiegel, Lafayette, CO (US); Aditya R. Dalvi, Broomfield, CO (US); Andrew J. Koert, Golden, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 133 days.

(21) Appl. No.: 17/591,951

(22) Filed: Feb. 3, 2022

(65) Prior Publication Data
US 2023/0240790 A1   Aug. 3, 2023

(51) Int. Cl.
| | | |
|---|---|---|
| *A61B 90/00* | (2016.01) | |
| *A61B 8/00* | (2006.01) | |
| *A61B 8/08* | (2006.01) | |
| *A61B 8/14* | (2006.01) | |
| *A61B 34/20* | (2016.01) | |

(Continued)

(52) U.S. Cl.
CPC ......... *A61B 90/37* (2016.02); *A61B 8/145* (2013.01); *A61B 8/466* (2013.01); *A61B 8/488* (2013.01); *A61B 8/523* (2013.01); *A61B 8/5253* (2013.01); *A61B 34/20* (2016.02); *G06T 11/00* (2013.01); *G06T 19/006* (2013.01); *A61B 2034/2063* (2016.02); *A61B 2090/365* (2016.02); *A61B 2090/372* (2016.02); *A61B 2090/378* (2016.02); *G06T 2210/41* (2013.01)

(58) Field of Classification Search
CPC ......... A61B 90/37; A61B 8/488; A61B 34/20; A61B 2034/2063; A61B 2090/365; A61B 2090/372; A61B 2090/378; A61B 8/145; A61B 8/466; A61B 8/523; A61B 8/5253; G06T 11/00; G06T 19/006; G06T 2210/41; G16H 40/60; G16H 50/20; G16H 30/40
See application file for complete search history.

(56) References Cited

U.S. PATENT DOCUMENTS

| | | |
|---|---|---|
| 5,810,008 A | 9/1998 | Dekel et al. |
| 6,019,724 A | 2/2000 | Gronningsaeter |

(Continued)

FOREIGN PATENT DOCUMENTS

| | | | | |
|---|---|---|---|---|
| CN | 103777840 A | * | 5/2014 | ............ A61B 6/145 |
| JP | 2011-182983 | | 9/2011 | |

(Continued)

OTHER PUBLICATIONS

Kim et al. "Feasibility Study of Precise Balloon Catheter Tracking and Visualization with Fast Photoacoustic Microscopy," Sensors, Oct. 2020, vol. 20, No. 19, pp. 5585.

(Continued)

*Primary Examiner* — Colin T. Sakamoto
(74) *Attorney, Agent, or Firm* — Sheridan Ross P.C.

(57) ABSTRACT

Systems, methods, and devices for providing an augmented display are provided. The system may comprise a display configured to display an image over an environment. At least one image may be received from an imaging device. The at least one image may be registered to a patient and displayed in the display. The display may display the image over the environment.

12 Claims, 8 Drawing Sheets

(51) Int. Cl.
*G06T 11/00* (2006.01)
*G06T 19/00* (2011.01)

(56) References Cited

U.S. PATENT DOCUMENTS

| | | | |
|---|---|---|---|
| 6,390,982 | B1 | 5/2002 | Bova et al. |
| 6,685,644 | B2 | 2/2004 | Seo et al. |
| 6,872,179 | B2 | 3/2005 | Kamiyama et al. |
| 7,203,277 | B2 | 4/2007 | Birkenbach et al. |
| 7,452,357 | B2 | 11/2008 | Vlegele et al. |
| 8,116,848 | B2 | 2/2012 | Shahidi |
| 9,055,883 | B2 | 6/2015 | Tgavalekos et al. |
| 9,204,863 | B2 | 12/2015 | Kumazawa |
| 9,211,163 | B1 | 12/2015 | Jaramaz et al. |
| 9,471,981 | B2 | 10/2016 | Arai et al. |
| 9,486,162 | B2 | 11/2016 | Zhuang et al. |
| 10,026,191 | B2 | 7/2018 | Accomando et al. |
| 10,383,693 | B2 | 8/2019 | Schmoll et al. |
| 10,568,535 | B2 | 2/2020 | Roberts et al. |
| 10,650,537 | B2 | 5/2020 | O'Connor et al. |
| 10,762,341 | B2 | 9/2020 | Vilsmeier et al. |
| 11,197,722 | B2 | 12/2021 | Tako et al. |
| 11,553,969 | B1 * | 1/2023 | Lang ............ G06T 7/0012 |
| 2004/0106869 | A1 | 6/2004 | Tepper |
| 2005/0085717 | A1 | 4/2005 | Shahidi |
| 2005/0261571 | A1 | 11/2005 | Willis et al. |
| 2006/0176242 | A1 * | 8/2006 | Jaramaz ............ G02B 27/017 345/7 |
| 2007/0021738 | A1 | 1/2007 | Hasser et al. |
| 2007/0239000 | A1 | 10/2007 | Emery et al. |
| 2007/0276234 | A1 | 11/2007 | Shahidi |
| 2008/0137927 | A1 * | 6/2008 | Altmann ............ A61B 8/12 382/131 |
| 2008/0247506 | A1 * | 10/2008 | Maschke ............ A61B 6/4476 378/15 |
| 2013/0158578 | A1 | 6/2013 | Ghodke et al. |
| 2014/0066766 | A1 * | 3/2014 | Stonefield ............ A61B 8/54 600/440 |
| 2015/0130799 | A1 | 5/2015 | Holzer et al. |
| 2015/0320395 | A1 * | 11/2015 | Sato ............ A61B 8/5207 600/455 |
| 2015/0359517 | A1 * | 12/2015 | Tan ............ A61B 8/4245 600/440 |
| 2016/0150217 | A1 | 5/2016 | Popov |
| 2018/0263706 | A1 | 9/2018 | Averbuch |
| 2018/0303463 | A1 | 10/2018 | Zanin et al. |
| 2018/0344411 | A1 | 12/2018 | Fahey et al. |
| 2019/0209130 | A1 | 7/2019 | Lieblich et al. |
| 2019/0219693 | A1 | 7/2019 | Lieblich et al. |
| 2019/0262082 | A1 * | 8/2019 | Krimsky ............ A61B 90/361 |
| 2019/0271771 | A1 | 9/2019 | Lieblich et al. |
| 2020/0159313 | A1 * | 5/2020 | Gibby ............ G06T 7/33 |
| 2020/0334897 | A1 | 10/2020 | Oved |
| 2021/0177524 | A1 | 6/2021 | Thienphrapa et al. |
| 2021/0192763 | A1 * | 6/2021 | Liu ............ H04N 13/239 |
| 2021/0196424 | A1 | 7/2021 | Shelton et al. |
| 2021/0386491 | A1 | 12/2021 | Shmayahu et al. |
| 2022/0079675 | A1 * | 3/2022 | Lang ............ G02B 30/52 |
| 2022/0104878 | A1 | 4/2022 | Weiss et al. |
| 2022/0189047 | A1 | 6/2022 | Lev-Tov et al. |

FOREIGN PATENT DOCUMENTS

| | | | |
|---|---|---|---|
| JP | WO 2009-136461 | 9/2011 | |
| KR | 10-2016-0026598 | 3/2016 | |
| WO | WO-2008038283 A2 * | 4/2008 | .......... A61B 6/4405 |
| WO | WO 2014/174069 | 10/2014 | |
| WO | WO 2016/018646 | 2/2016 | |
| WO | WO-2016026053 A1 * | 2/2016 | ............ A61B 34/10 |
| WO | WO 2016/082017 | 6/2016 | |
| WO | WO 2020/243425 | 12/2020 | |

OTHER PUBLICATIONS

Srivastava et al. "Unsupervised Deep Learning based Longitudinal Follicular Growth Tracking during IVF Cycle using 3D Transvaginal Ultrasound in Assisted Reproduction," IEEE, 2021 43rd Annual International Conference of the IEEE Engineering in Medicine & Biology Society (EMBC), Nov. 2021, pp. 3209-3212.

Yeung et al. "ImplicitVol: Sensorless 3D Ultrasound Reconstruction with Deep Implicit Representation," arxiv.org, Sep. 24, 2021, 11 pages.

Invitation to Pay Additional Fees for International (PCT) Patent Application No. PCT/IB2023/050792, dated Apr. 6, 2023, 15 pages.

International Search Report and Written Opinion for International (PCT) Patent Application No. PCT/IB2023/050792, dated May 30, 2023, 21 pages.

International Search Report and Written Opinion for International (PCT) Patent Application No. PCT/IB2023/050646, dated May 15, 2023, 10 pages.

International Search and Written Opinion for International (PCT) Patent Application No. PCT/IB2023/050675, dated Apr. 26, 2023, 11 pages.

International Search and Written Opinion for International (PCT) Patent Application No. PCT/IB2023/050678, dated Apr. 24, 2023, 14 pages.

Official Action for U.S. Appl. No. 17/591,919, dated Apr. 5, 2024 10 pages.

Official Action for U.S. Appl. No. 17/591,904, dated Sep. 7, 2023 16 pages.

Notice of Allowance for U.S. Appl. No. 17/591,904, dated Jan. 10, 2024 8 pages.

Official Action for U.S. Appl. No. 17/591,919, dated Jul. 18, 2024 12 pages.

* cited by examiner

SYSTEMS, METHODS, AND DEVICES FOR PROVIDING AN AUGMENTED DISPLAY

FIELD

The present technology generally relates to imaging and image processing, and relates more particularly to providing an augmented display.

BACKGROUND

Imaging devices may be used by a medical provider for diagnostic and/or therapeutic purposes. Images may be obtained from imaging devices using different modalities at various times (e.g., preoperatively, intraoperatively, postoperatively). Such images may also contain various information (e.g., soft tissue and/or hard tissue) based on the nature of the imaging device used to capture the images.

SUMMARY

Example aspects of the present disclosure include:

A system for providing an augmented display according to at least one embodiment of the present disclosure comprises an image device; a display configured to display an image over an environment; a processor; and a memory storing data for processing by the processor, the data, when processed, causing the processor to: receive at least one image from the image device; register the at least one image to a patient to yield at least one registered image; and display the at least one registered image in the display, the display displaying the image over the environment.

Any of the aspects herein, wherein the image device comprises an ultrasound image device.

Any of the aspects herein, further comprising a navigation system configured to use the at least one registered image for navigation of at least one surgical instrument, wherein the memory stores further data for processing by the processor that, when processed, causes the processor to: generate instructions for navigating the at least one surgical instrument based on the at least one registered image.

Any of the aspects herein, wherein the display comprises a headset display. Any of the aspects herein, wherein the at least one image is displayed semi-transparently with respect to the environment.

Any of the aspects herein, wherein the at least one image is overlaid opaquely over the environment.

Any of the aspects herein, wherein the memory stores further data for processing by the processor that, when processed, causes the processor to: receive at least one updated image from the image device; register the at least one updated image to the patient to yield at least one updated registered image; and replace the at least one registered image with the at least one updated registered image in the display.

Any of the aspects herein, wherein the memory stores further data for processing by the processor that, when processed, causes the processor to: receive at least one updated image from the image device; compare the at least one image to the at least one updated image; register the at least one updated image to the patient to yield at least one updated registered image when a difference between the at least one image and the at least one updated image is detected; and replace the at least one registered image with the at least one updated registered image in the display.

Any of the aspects herein, wherein the memory stores further data for processing by the processor that, when processed, causes the processor to: receive pose information of the image device for each of the at least one image, the pose information comprising a position and orientation of the image device; input the at least one image and the pose information to a reconstruction model, the reconstruction model configured to generate a three-dimensional representation of one or more anatomical elements based on the at least one image and the pose information; and receive, from the reconstruction model, the three-dimensional representation of the one or more anatomical elements based on the at least one image and the pose information; and display the three-dimensional representation in the display.

Any of the aspects herein, wherein displaying the at least one registered image displays the at least one registered image in a doppler mode.

Any of the aspects herein, wherein displaying the at least one registered image displays the at least one registered image in real-time.

Any of the aspects herein, wherein the memory stores further data for processing by the processor that, when processed, causes the processor to: receive information about an environment visible in the display, the information comprising a position and an orientation of the patient; and display one or more of the at least one registered image correlating to the position and orientation of the patient.

A device for providing an augmented display according to at least one embodiment of the present disclosure comprises a processor; and a memory storing data for processing by the processor, the data, when processed, causing the processor to: receive at least one image from an image device; register the at least one image to a patient to yield a at least one registered image; and display the at least one registered image in the display.

Any of the aspects herein, wherein the image device comprises an ultrasound image device.

Any of the aspects herein, further comprising a navigation system configured to use the at least one registered image for navigation of at least one surgical instrument, wherein the memory stores further data for processing by the processor that, when processed, causes the processor to: generate instructions for navigating the at least one surgical instrument based on the at least one registered image.

Any of the aspects herein, wherein the at least one image is displayed semi-transparently with respect to an environment.

Any of the aspects herein, wherein the memory stores further data for processing by the processor that, when processed, causes the processor to: receive at least one updated image; register the at least one updated image to the patient to yield at least one updated registered image; and replace the at least one registered image with the at least one updated registered image.

Any of the aspects herein, wherein the memory stores further data for processing by the processor that, when processed, causes the processor to: receive at least one updated image; compare the at least one image to the at least one updated image; register the at least one updated image to the patient to yield at least one updated registered image when a difference between the at least one image and the at least one updated image is detected; and replace the at least one registered image with the at least one updated registered image.

Any of the aspects herein, wherein the memory stores further data for processing by the processor that, when processed, causes the processor to: receive pose information for each of the at least one image, the pose information comprising a position and orientation of the image device when the at least one image is obtained; input the at least one image and the pose information to a reconstruction model, the reconstruction model configured to generate a three-dimensional model representation of one or more anatomical elements based on the at least one image and the pose information; receive, from the reconstruction model, the three-dimensional model representation of the one or more anatomical elements based on the at least one image and the pose information; and display the three-dimensional model representation in a display.

A system for providing an augmented display according to at least one embodiment of the present disclosure comprises an image device; a navigation system; a display configured to display one or more images overlaid over an environment; a processor; and a memory storing data for processing by the processor, the data, when processed, causing the processor to: receive at least one image; register the at least one image to a patient to yield at least one registered image; display the at least one registered image over an environment in the display; and generate instructions for navigating the at least one surgical instrument based on the at least one registered image.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided herein below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
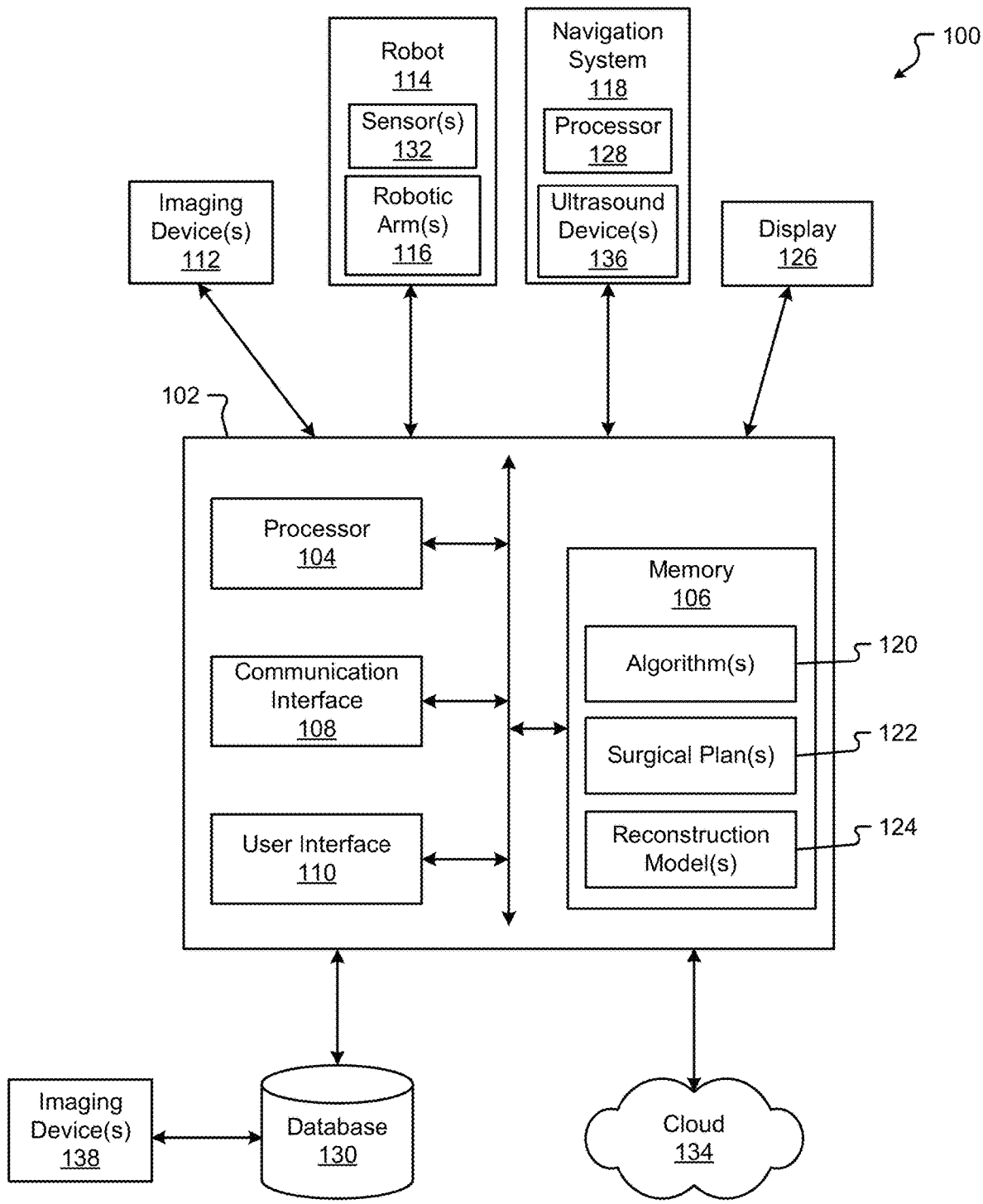
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions or algorithms may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10× Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 4000-series processors, AMD Radeon RX 6000-series processors, AMD Radeon RX 7000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Navigation systems may be used to provide navigation for a surgeon or a robotic system during a surgical procedure. Such systems may provide navigation relative to, for example, a preoperative image (e.g., a magnetic resonance image (MRI) or computed tomography (CT) image) depicting one or more anatomical elements. However, during a surgical procedure, if the one or more anatomical elements move or shift, then the navigation system may no longer be accurate and may require updating.

According to at least one embodiment of the present disclosure, ultrasound imaging can be used with the navigation system to provide updated imaging of the one or more anatomical elements, which can provide updated information about a pose of the one or more anatomical elements. The pose includes a position and an orientation. The updated images may also be aligned with the preoperative image. Thus, integration of ultrasound and navigation can provide real-time updated imaging of one or more anatomical elements to ensure that the navigation system is navigating relative to a current pose of the one or more anatomical elements.

There are also a number of advantages that combining ultrasound imaging with surgical navigation can offer. Ultrasound does not emit harmful radiation and thus, can be used continuously during a surgical procedure without exposing a patient and a surgical team to radiation. This results in a safer environment for the patient, surgeon, and surgical team. Ultrasound may also be helpful to track certain objects and/or anatomical elements (e.g., soft tissue) as compared to, for example, X-ray based imaging, which may be better suited for other objects/anatomical elements (e.g., hard tissue, manmade objects, etc.). Ultrasound with navigation can be used for multiple applications such as, for example, cranial and/or spinal procedures. Current imaging and navigation can overlay an ultrasound image over a pre-operative image (e.g., an MRI or CT image); take measurements on ultrasound images; and/or capture a series of images and play through the images.

In at least one embodiment, ultrasound navigation may be used for, for example, three-dimensional ultrasound navigation; electromagnetic navigated ultrasound; augment reality; using artificial intelligence to merge ultrasound with pre-operative imaging for real-time brain shift compensation; reconstructing patient anatomy of interest (e.g., vascular and/or tumor); patient auto-registration; tumor ablation confirmation; tracking hardening of biologics; track size of tool (e.g., a balloon) between anatomical elements (e.g., vertebrae); and/or segmental tracking.

Embodiments of the present disclosure provide technical solutions to one or more of the problems of (1) providing image(s) in an augmented display; (2) providing real-time updates of one or more anatomical elements to an augmented display; (3) providing navigation after movement of one or more anatomical elements; and (4) increasing patient, surgeon, and surgical team safety.

Turning first to FIG. 1, a block diagram of a system 100 according to at least one embodiment of the present disclosure is shown. The system 100 may be used to provide an augmented display, which may be used for navigation, and/or carry out one or more other aspects of one or more of the methods disclosed herein. The system 100 comprises a computing device 102, one or more imaging devices 112, a robot 114, a navigation system 118, a display 126, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, the display 126, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, the display 126, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 400, 500, 600, 700 described herein, or of any other methods. The memory 106 may store, for example, one or more algorithms 120, one or more surgical plans 122, and/or one or more reconstruction models 124. Such algorithms may, in some embodiments, be organized into one or more applications, modules, packages, layers, or engines. Alternatively or additionally, the memory 106 may store other types of data (e.g., machine learning models, artificial neural networks, etc.) that can be processed by the processor 104 to carry out the various method and features described herein. Thus, although various components of memory 106 are described as algorithms, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, the display 126, and/or the cloud 134. The reconstruction models 124 may be trained (as described with respect to FIG. 2), then made available to the computer device 102 to enable generating three-dimensional representations of one or more objects, anatomical elements, tools, and/or instruments.

The computing device 102 may also comprise a communication interface 108. The communication interface 108 may be used for receiving image data or other information from an external source (such as the imaging device 112, the robot 114, the navigation system 118, the display 126, the database 130, the cloud 134, and/or any other system or component not part of the system 100), and/or for transmitting instructions, images, or other information to an external system or device (e.g., another computing device 102, the imaging device 112, the robot 114, the navigation system 118, the display 126, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The system 100 may include a display 126. The display 126 may communicate with the computing device 102 or the processor 104 of the computing device to receive and display at least one image. It will be appreciated that in some embodiments, the display 126 can communicate with any component of the system 100 or any component external to the system 100. In some embodiments, the display 126 is an augmented display in which an environment is visible through at least a portion of the display and the at least one image may be displayed as an overlay on the environment. In such embodiments, the display 126 may comprise a headset worn by a user. The headset may comprise a screen through which the environment is visible to the user and on which the at least one image may be displayed on. In some embodiments, the headset may display at least one image or information corresponding to an object, anatomical element, portion of a patient, tool, and/or an instrument in a field of view of the headset. The headset may be beneficial in, for example, providing information to a user such as a surgeon during a surgical procedure. For example, the headset may display one or more steps of the surgical plan 122. In another example, a three-dimensional representation of a tumor to be ablated may be displayed overlaid onto a surgical site of a patient. In such examples, the three-dimensional representation of the tumor may be updated as the ablation procedure progresses.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. The imaging device 112 may be capable of capturing a two-dimensional image, a series of two-dimensional images, a three-dimensional image, and/or a series of three-dimensional images to yield the image data.

The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient.

In some embodiments, the imaging device 112 may comprise more than one imaging device 112. For example, a first imaging device may provide first image data and/or a first image at a first time, and a second imaging device may provide second image data and/or a second image at the first time or at a second time after the first time. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

In some embodiments, the imaging device 112 may comprise a source and a detector. In such embodiments, the imaging device 112 may be an ultrasound device or an x-ray imaging device. In some embodiments, the source and the detector may be in separate housings or are otherwise physically separated. In such embodiments, the source may be oriented by a first robotic arm and the detector may be oriented by a second robotic arm, as will be described in more detail below. In other embodiments, the source and the detector may be in the same housing. The source may be configured to emit a wave and the detector may be configured to receive a signal indicative of the emitted wave. The detector may also be configured to save a plurality of image datasets to, for example, the memory 106.

In some embodiments, the imaging device 112 may be a first imaging device 112 and the system 100 may include a second imaging device 138, which may be the same as or similar to the imaging device 112. The second imaging device 138 may be in communication with the database 130. The second imaging device 138 may provide preoperative images, which may be stored in the database 130 for use at a later time. For example, a preoperative image of a patient may be obtained at a date prior to a surgical procedure. The preoperative image may be stored in the database 130 (whether as part of the surgical plan 122 or separately) and retrieved anytime thereafter. In other instances, the second imaging device 138 may provide a preoperative image prior to a start of a surgical procedure. The second imaging device 138 in some embodiments may use a different modality than the first imaging device 112. For example, the second imaging device 138 may be a CT or MRI scanner and the first imaging device 112 may be an ultrasound device.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure.

The robot 114 may comprise one or more robotic arms 116. The robotic arms may be controlled in a single, shared coordinate space, or in separate coordinate spaces. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components such as, for example, the source and the detector, one robotic arm 116 may hold the source, and another robotic arm 116 may hold the detector. Each robotic arm 116 may be accurately positionable independently of the other robotic arm (e.g., the detector can be positioned or oriented independently of the source). In some embodiments, one robotic arm 116 may orient the source at a first pose across from the detector oriented by another robotic arm 116 at a second pose. In some embodiments, the source may remain at the same pose while the detector is oriented at different poses. In other embodiments, the detector may remain at the same pose while the source is oriented at different poses. In still other embodiments, both the detector and the source may each be oriented at different poses.

The robot 114, together with the robotic arm 116, may have, for example, one, two, three, four, five, six, seven, or more degrees of freedom. Further, the robotic arm 116 may be positioned or positionable in any pose, plane, and/or focal point. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm). Each sensor 132 may be any kind of sensor 132 for measuring the pose in space of the robotic arm 116. The sensor 132 may comprise one or more or any combination of components that are electrical, mechanical, electro-mechanical, magnetic, electromagnetic, or the like. The sensor 132 may comprise, but is not limited to, one or more of a linear encoder, a rotary encoder, a capacitor, and/or an accelerometer. In some embodiments, the sensor 132 may include a memory for storing sensor data. In still other examples, the sensor 132 may output signals (e.g., sensor data) to one or more sources (e.g., the computing device 102, the navigation system 118, and/or the robot 114).

The sensor 132 may be integrated internally into the robotic arm 116 or otherwise positioned inside of the robotic arm. In some embodiments, the sensor 132 is positioned inside a joint of the robotic arm 116. The sensor 132 may include a plurality of sensors and each sensor may be positioned at the same location or a different location as any other sensor. For example, a sensor 132 may be positioned in one or more joints of the robotic arm 116. It will be appreciated that in some embodiments the sensor 132 can be positioned at or on any component of the system 100 or environment (e.g., on any portion of the navigation system 118, the robot 114, the robotic arm 116, and/or any other component at the surgical site).

The sensor 132 may be operable to sense and/or monitor the pose (e.g., position and orientation), position, or orientation of any portion of the robotic arm 116. The sensor 132 may send the data to the computing device 102 at any time, whether continuously, at a time interval, in response to an input from a user requesting the data, or a change in pose, position, or orientation of the robotic arm 116. Further, in some embodiments, the sensor 132 may send data to the computing device 102 to display on the user interface 110.

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

In some embodiments, electromagnetic sensor(s) may be used to track any component of the system 100 including, for example, the imaging device 112. The electromagnetic sensor(s) may be used by the navigation system 118 to track a corresponding component. For example, an electromagnetic sensor may be disposed on or integrated with an ultrasound transducer for tracking a pose of the transducer in real-time. In some embodiments, the electromagnetic sensor may be removable.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker or an electromagnetic sensor attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

In some embodiments, an ultrasound device 136 may be integrated with the navigation system 118 in which images from the ultrasound device may be used by the navigation system 118 for navigation. In some embodiments, the hardware for an ultrasound device 136 may be directly integrated with the navigation system 118 hardware. In other embodiments, the ultrasound device 136 may be a separate component. Whether directly integrated or combined as separate components, a processor such as the processor 104 or a processor 128 of the navigation system 118 may receive data from the ultrasound device 136 and automatically process such data for use by the navigation system 118.

In embodiments using an integrated navigation system 118 and ultrasound device 136, the navigation system 118 may navigate a surgeon or robotic system relative to a preoperative image (e.g., MRI or CT image(s)) depicting one or more anatomical elements, and an ultrasound probe may provide real-time or live imaging of the one or more anatomical elements during a surgical procedure. The preoperative image(s) may be obtained from, for example, the database 130 and/or the second imaging device 138. The real-time or live image(s) obtained from the ultrasound device 136 can be aligned with preoperative image(s) (e.g., MRI or CT images) to confirm or—in instances where an anatomical element has moved—update a pose of the anatomical element and surrounding anatomical elements. The navigation system 118 may then provide navigation based on the updated pose of the anatomical element(s). Thus, the ultrasound device 136 enables the navigation system 118 to continue to navigate when one or more anatomical elements shift or move, either in space or relative to one another. In some instances, the real-time or live image(s) can be used to generate a three-dimensional ultrasound representation that can be overlaid onto a preoperative three-dimensional representation generated from preoperative image(s). The navigation system 118 may then navigate based on the three-dimensional ultrasound representation. In some instances, the real-time or live image(s) can be used to generate a three-dimensional ultrasound representation that can be overlaid onto a preoperative two-dimensional image that depicts the anatomical elements.

The combined navigation system 118 and ultrasound device 136 may be used in various applications. For example, the combined navigation system 118 and ultrasound device 136 may be used to view a progress of or confirm a tumor ablation, while the tumor is in the process of being ablated. In such examples, a navigated ultrasound probe may be used to obtain a current ultrasound image of an ablated tumor area, which may be compared to a preoperative image obtained prior to the ablation procedure. In another example, the combined navigation system 118 and ultrasound device 136 may be used to auto-register and/or reregister a patient. In such examples, images obtained from the ultrasound device 136 may be automatically aligned and correlated to preoperative images. In still another example, the combined navigation system 118 and ultrasound device 136 may be used generate a three-dimensional representation of one or more anatomical elements based on a set of images and corresponding pose information that can be used by the navigation system 118 for navigation, as will be described in detail in FIGS. 3-6.

The database 130 may store, for example, the one or more algorithms 120, the one or more surgical plans 122 (including, for example, preoperative image(s); steps for orienting the imaging device 112 at one or more poses; etc.); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the model architecture 200 and/or methods 400, 500, 600, 700 described herein. The system 100 or similar systems may also be used for other purposes.

Figure 2:
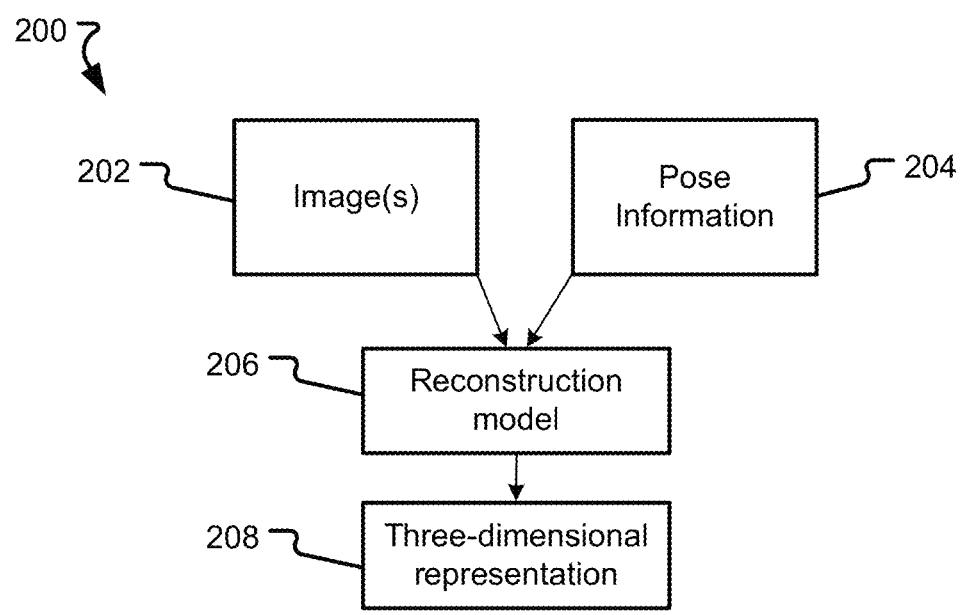
FIG. 2 is a flowchart according to at least one embodiment of the present disclosure.

Turning to FIG. 2, an example of a model architecture 200 that supports methods and systems (e.g., Artificial Intelligence (AI)-based methods and/or system) for generating a three-dimensional representation of one or more anatomical elements is shown. It will be appreciated that a three-dimensional representation may be generated for one or more objects, instruments, and/or tools.

At least one image 202 may be obtained by an imaging device such as the imaging device 112. In some embodiments the imaging device may be an ultrasound device. The at least one image 202 may depict one or more objects and/or one or more anatomical elements of, for example, a patient. The at least one image 202 may be obtained at any time such as, for example, preoperatively, intraoperatively, or postoperatively.

Pose information 204 corresponding to the at least one image 202 may be obtained. The pose information 204 may be, for example, separate from the set of images and may comprise coordinates of the imaging device when a corresponding image is obtained. The pose information 204 may be useful for determining a spatial relationship between the set of images 202. In some embodiments, the pose information 204 may be obtained from a navigation system such as the navigation system 118 which may be configured to track the imaging device 112. The imaging device 112 may be tracked using, for example, reference markers or electromagnetic trackers. In other embodiments, the imaging device 112 may be supported by a robotic arm such as the robotic arm 116 and pose information may be obtained from the sensors 132 integrated with or disposed on the robotic arm 116. The sensors 132 may be configured to track, among other things, a pose of the robotic arm 116. More specifically, a pose of an end of the robotic arm 116 may be tracked, or may be determined from a pose of any portion of the robotic arm 116. The pose of the robotic arm 116 may correlate to a pose of the imaging device 112 when the imaging device 112 is oriented by the robotic arm 116.

The at least one image 202 and the pose information 204 are received as input by a reconstruction model 206, which may be the same as or similar to the reconstructions model 124 stored in the memory 106. The reconstruction model 206 may be trained using historical image(s) and/or historical pose information. In other embodiments, the reconstruction model 206 may be trained using the at least one image 202 and/or the pose information 204. In such embodiments, the reconstruction model 206 may be trained prior to inputting the at least one image 202 and the pose information 204 into the reconstruction model 206 or may be trained in parallel with inputting the at least one image 202 and the pose information 204, as will be described in detail with respect to FIG. 3.

The reconstruction model 206 may be configured to generate a three-dimensional representation 208 of the one or more anatomical elements. Generating the three-dimensional representation 208 may include determining a surface representation or virtual boundary of the one or more anatomical elements depicted in the at least one image 202 based on the corresponding pose information. More specifically, in some embodiments, each image may be positioned adjacent to another image based on the respective corresponding pose information and a surface representation may be formed based the relative position of surfaces depicted in each image. In some embodiments, the surface representation may be a virtual mesh. The virtual mesh may comprise, for example, a set of polygonal faces that, when taken together, form a surface covering of a virtual object. The set of polygonal faces may be connected at their edges and vertices to define a shape of the virtual object.

Figure 3A:
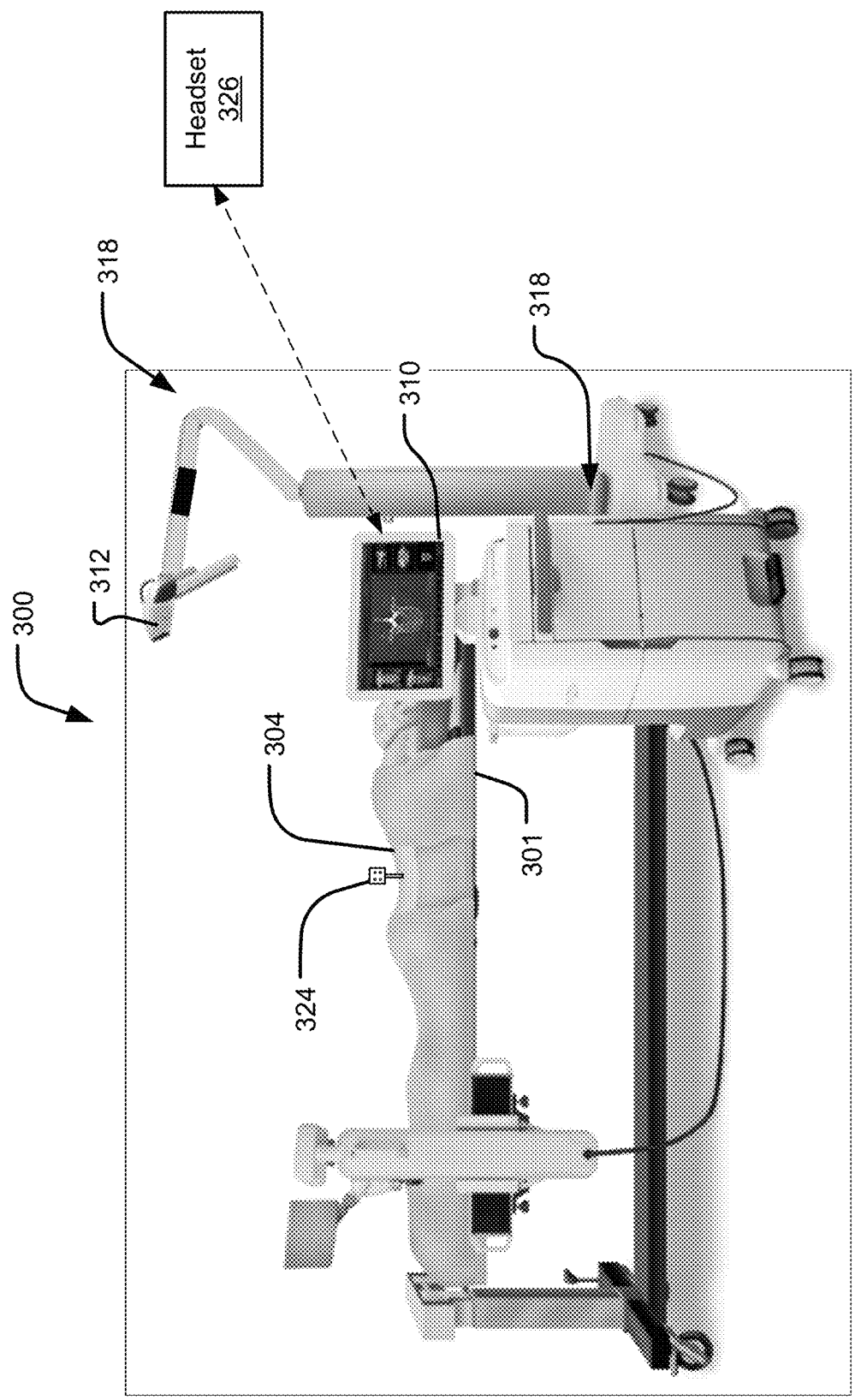
FIG. 3A is a schematic diagram of an operating room according to at least one embodiment of the present disclosure.

Turning to FIG. 3A, at least a portion of a surgical room 300 is illustrated including a computing device 302 (which may be the same as or similar to the computing device 102), an operating table 301, a patient 304 laying prone on the table 301, and a navigation system 318. In this embodiment, the navigation system 318 (which may be the same as or similar to the navigation system 118 described above) comprises an imaging device 312 (which may be the same as or similar to the imaging device 112 described above), as well as a user interface 310 (e.g., a display), which may be the same as or similar to the user interface 110 described above. A tracking device 324 may be disposed on the patient 304 and tracked by the navigation system 318. A headset 326 may be in communication with the navigation system 318, the computing device 302, and/or any other component.

Figure 3B:
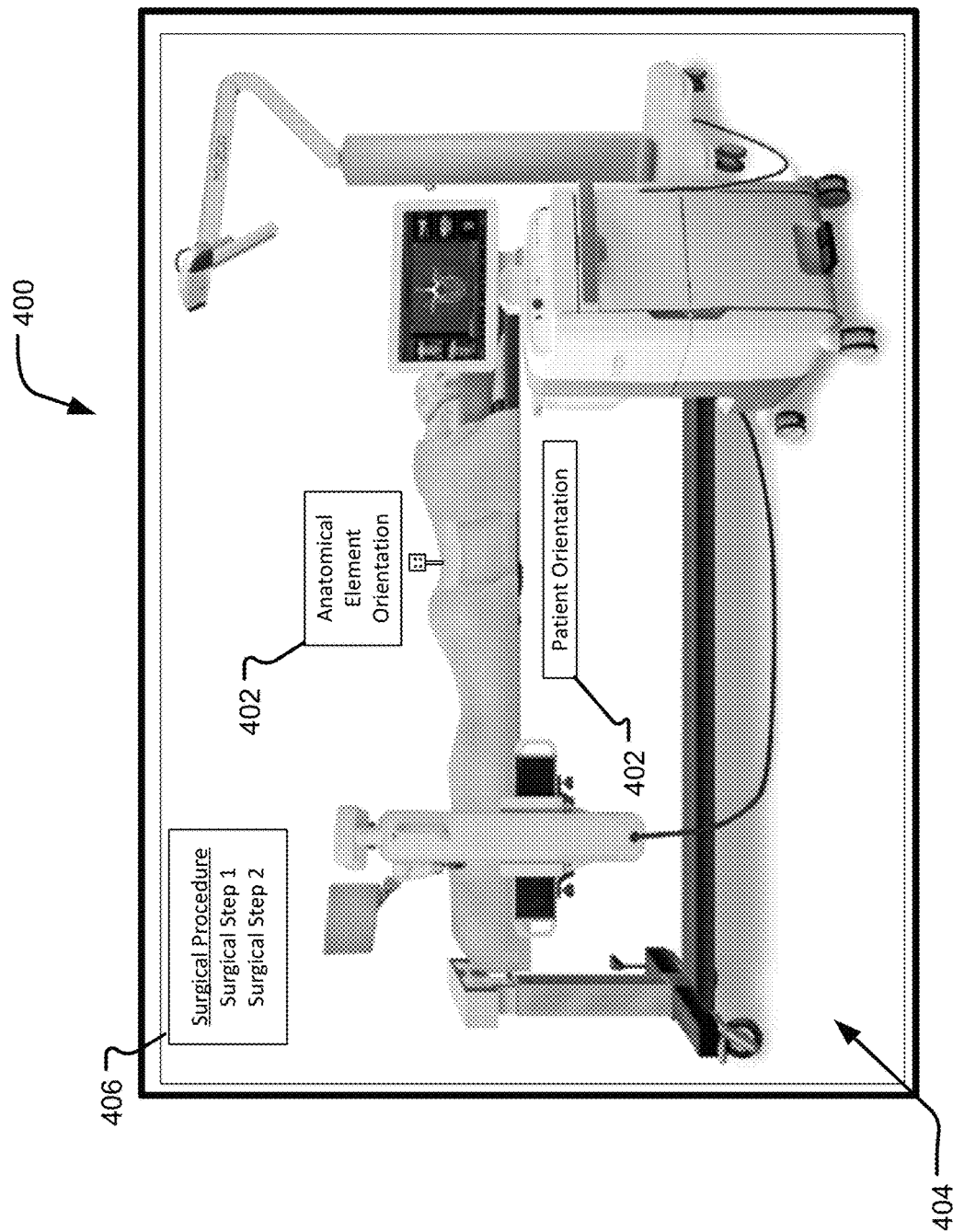
FIG. 3B is a schematic diagram of a field of view of a display according to at least one embodiment of the present disclosure.

Turning to FIG. 3B, a field of view 400 of the headset 326 is illustrated. The headset 326 may be the same as or similar to the augmented display described above in which an environment 404 is visible through at least a portion of the display and the at least one image may be displayed as an overlay 402 on the environment. The headset may 326 comprise a screen through which the environment 404 is visible to the user and on which the at least one image may be displayed on. In some embodiments, the headset 326 may display at least one image or information such as the information shown as an overlay 402 corresponding to an object, anatomical element, portion of a patient, tool, and/or an instrument in a field of view of the headset. The overlay may be opaque or semi-transparent. The headset 326 may be beneficial in, for example, providing information to a user such as a surgeon during a surgical procedure. For example, the headset may display one or more steps 406 of the surgical plan 122.

Figure 4:
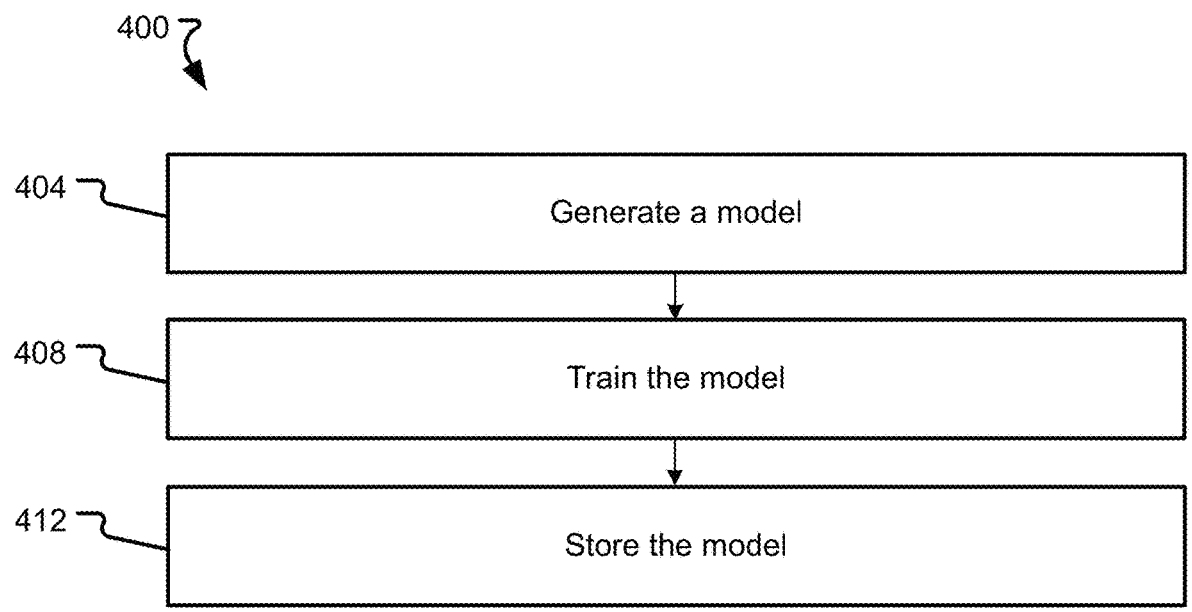
FIG. 4 is a flowchart according to at least one embodiment of the present disclosure.

Turning to FIG. 4, a method 400 that may be used, for example, for generating a model is provided.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as the algorithm 120.

The method 400 comprises generating a model (step 404). The model may be the reconstruction model 206, 124. A processor such as the processor 104, 128 may generate the model. The model may be generated to facilitate and enable, for example, generating of a three-dimensional representation of one or more anatomical elements and/or objects.

The method 400 also comprises training the model (step 408). In embodiments where the model is trained prior to a surgical procedure, the model may be trained using historical data from a number of patients. In some embodiments, the historical data may be obtained from patients that have similar patient data to a patient on which a surgical procedure is to be performed. In other embodiments, the historical data may be obtained from any patient.

In other embodiments, the model may be trained in parallel with use of another model. Training in parallel may, in some embodiments, comprise training a model using input received during, for example, or prior to a surgical procedure, while also using a separate model to receive and act upon the same input. Such input may be specific to a patient undergoing the surgical procedure. In some instances, when the model being trained exceeds the model in use (whether in efficiency, accuracy, or otherwise), the model being trained may replace the model in use. Such parallel training may be useful, for example, in situations, where a model is continuously in use (for example, when an input (such as, for example, an image) is continuously updated) and a corresponding model may be trained in parallel for further improvements.

In some embodiments, it will be appreciated that the model trained using historical data may be initially used as a primary model at a start of a surgical procedure. A training model may also be trained in parallel with the primary model using patient-specific input until the training model is sufficiently trained. The primary model may then be replaced by the training model.

The method 400 also comprises storing the model (step 412). The model may be stored in memory such as the memory 106 for later use. In some embodiments, the model is stored in the memory when the model is sufficiently trained. The model may be sufficiently trained when the model produces an output that meets a predetermined threshold, which may be determined by, for example, a user, or may be automatically determined by a processor such as the processor 104.

The present disclosure encompasses embodiments of the method 400 that comprise more or fewer steps than those described above, and/or one or more steps that are different than the steps described above.

Figure 5:
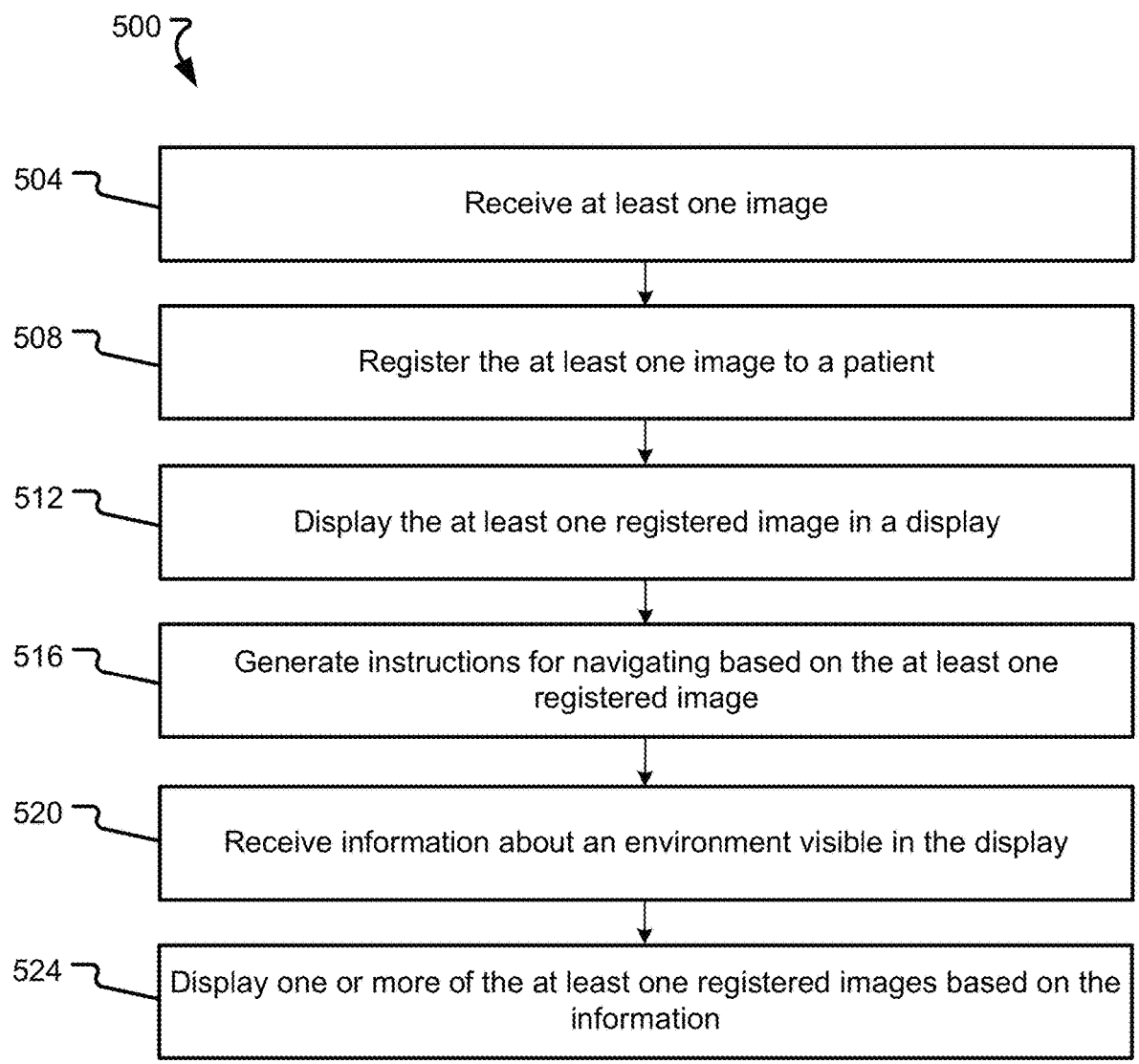
FIG. 5 is a flowchart according to at least one embodiment of the present disclosure.

FIG. 5 depicts a method 500 that may be used, for example, for providing an augmented display.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing instructions stored in a memory such as the memory 106. The instructions may correspond to one or more steps of the method 500 described below. The instructions may cause the processor to execute one or more algorithms, such as the algorithm 120.

The method 500 comprises receiving at least one image (step 504). The at least one image may be the same as or similar to the at least one image 202. The at least one image may be obtained from an imaging device such as the imaging device 112 or an ultrasound device such as the ultrasound device 136. In some embodiments, the ultrasound device is integrated with a navigation system such as the navigation system 118. The at least one image may comprise one or more two-dimensional images, one or more three-dimensional images, or a combination of one or more two-dimensional images and one or more three-dimensional images. The at least one image may depict one or more anatomical elements. In some embodiments, the at least one image may contain hard tissue information about the one or more anatomical elements. In other embodiments, the at least one image may contain soft tissue information about the one or more anatomical elements.

The method 500 also comprises registering the at least one image to a patient (step 508). Registering the at least one image to the patient may comprise automatically aligning and correlating the at least one image to preoperative image(s) of the patient (which may be obtained from, for example, the database 140). The preoperative image(s) may be obtained from, for example, a database such as the database 130 and/or an imaging device such as imaging device 112 and/or imaging device 138. More specifically, the aligning may be based at least in part on a corresponding one or more poses of the imaging device from which the at least one image was obtained. For example, a position of one or more anatomical features in the at least one image may be calculated based on the known position and/or orientation of the imaging device when each image was taken, and matched to a position of one or more anatomical features in the preoperative image(s) (calculated based on the known position and/or orientation of an imaging device when the preoperative image(s) were taken) and the second images may be compared to determine if the one or more anatomical features are present therein. In other examples, feature recognition may be used to identify a feature of an anatomical feature in each of the at least one image and the preoperative image(s), based upon which the at least one image and the preoperative image(s) may be matched to each other. For example, a contour of a vertebrae may be identified in the at least one image and the corresponding preoperative image. When the alignment is complete, the alignment provides a relative orientation and a relative position of the anatomical feature in the at least one image to the preoperative image(s).

In some embodiments, the alignment enables mapping of a first image space corresponding to the preoperative image(s) to a second image space corresponding to the at least one images, and from the second image space to the patient space, and thus enables a determination of the relative positions and/or orientations of the patient's anatomical features between a first orientation of the patient (e.g., when the preoperative image(s) were taken) and a second orientation of the patient (e.g., when the at least one image was taken).

The method 500 also comprises displaying the at least one registered image in a display (step 512). The display may be the same as or similar to the display 126. In some embodiments, the display is an augmented display through which an environment may be visible to a user. In such embodiments, the at least one registered image may be displayed over the environment. Such augmented displays are useful in applications, such as, a surgical procedure where information about a target anatomical element or instrument may be displayed to a surgeon, for example. In other examples, pertinent patient data and/or steps of a surgical plan such as the surgical plan 122 may be displayed. In still other examples, the at least one registered image may provide information about an anatomical element such as, for example, soft tissue information. The at least one registered image may be displayed in real-time or near real-time to provide current information to a user such as a surgeon or other medical provider. In some embodiments, the at least one registered image is displayed semi-transparently with respect to the environment. In other embodiments, the at least one registered image may be displayed or overlaid opaquely over the environment. In still other embodiments, the at least one registered image may be displayed in a doppler mode.

The method 500 also comprises generating instructions for navigating based on the least one registered image (step 516). A navigation system such as the navigation system 118 may provide the navigation. The instructions may be generated for navigating one or more instruments, tools, and/or anatomical elements, by a user such as a surgeon or other medical provide or by a robotic arm such as the robotic arm 116. The instructions may be generated by a processor such as the processor 104, 128 (whether of the navigation system or as a separate component). The instructions may be machine readable data and transmitted to, for example, the robotic arm 116 to cause the robotic arm 116 to execute the instructions. The instructions may also be human readable data and may be displayed on a user interface such as the user interface 110 for instructing the user.

The method 500 also comprises receiving information about an environment visible in a field of view of the display (step 520). The information about the environment may include information about an object, a portion of the patient, one or more anatomical elements, instruments, and/or tools visible in the field of view. The information may also, in some instances, include a position and/or orientation of a patient. In some embodiments, the information may include a pose, position, or orientation of such objects, anatomical elements, tools, instruments, portions of the patient visible in the field of view of the display. In some embodiments, feature recognition may be used to identify different objects visible within the field of view of the display. In other embodiments, a user may input various objects visible within the field of view of the display.

The method 500 also comprises displaying one or more of the at least one registered images based on the information about the environment (step 524). In some embodiments, the information includes a position and orientation of the patient. Such information may be useful to determine which portion of the patient is within the field of view of the display. In other embodiments, the information includes one or more objects, anatomical elements, instruments, and/or tools within the field of view of the display. Displaying the one or more of the at least one registered images may comprise identifying the images of the at least one registered images that correlate to the patient and/or one or more objects visible in the field of view of the display. For example, an anatomical element visible in the field of view of the display and images depicting the anatomical element may be identified based on the registration, and displayed on the display. In some embodiments, a three-dimensional representation generated using, for example, the method 700 described below, may be identified and displayed on the display.

It will be appreciated that in some embodiments, the steps 520 and 524 may be continuously repeated, performed in different orders than depicted, etc. For example, in embodiments where the display is an augmented display, objects, tools, anatomical elements, and/or instruments within the field of view of the display may change as a user turns his or her head. The at least one image being displayed may be updated as the field of view of the display changes.

The present disclosure encompasses embodiments of the method 500 that comprise more or fewer steps than those described above, and/or one or more steps that are different than the steps described above.

Figure 6:
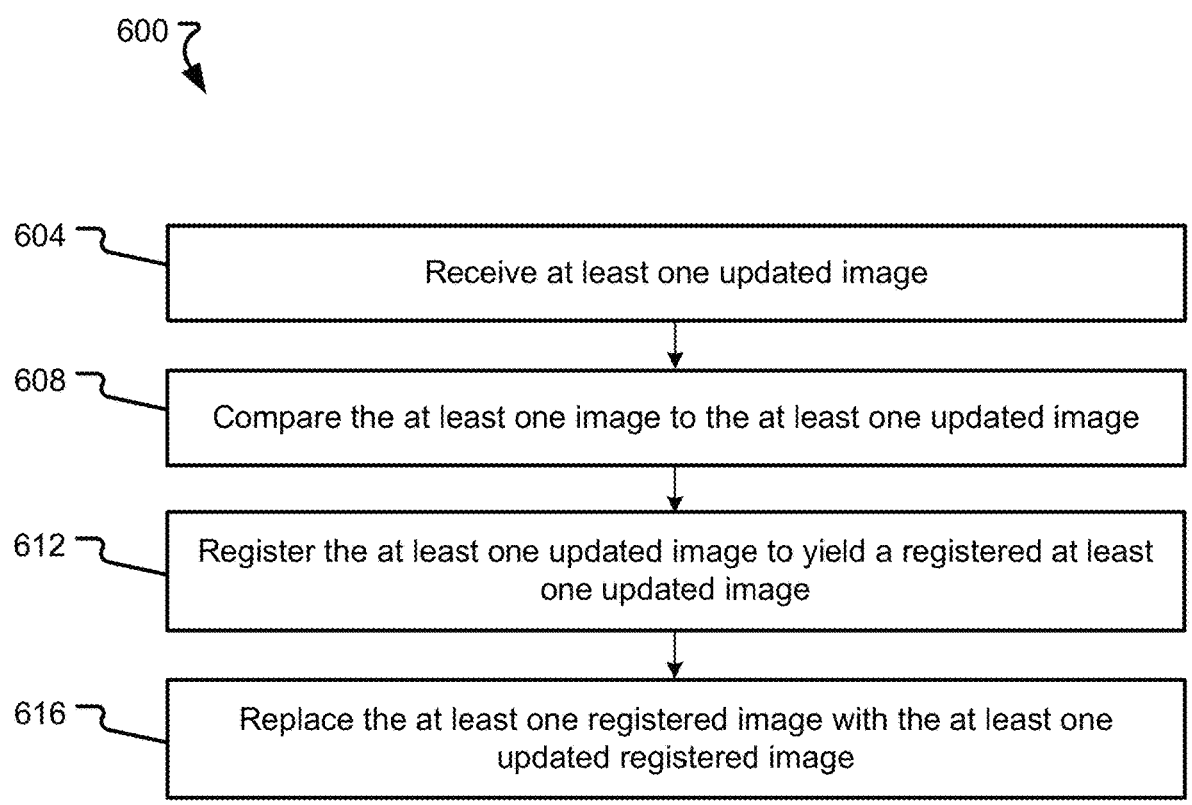
FIG. 6 is a flowchart according to at least one embodiment of the present disclosure.

FIG. 6 depicts a method 600 that may be used, for example, for updating the at least one registered image.

The method 600 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 600. The at least one processor may perform the method 600 by executing instructions stored in a memory such as the memory 106. The instructions may correspond to one or more steps of the method 600 described below. The instructions may cause the processor to execute one or more algorithms, such as the algorithm 120.

The method 600 comprises receiving at least one updated image (step 604). The step 604 may be the same as or similar to the step 504 of method 500 described above. The at least one updated image may be received from the same imaging device as the at least one image. In other instances, the at least one updated image may be received from a different imaging device as the at least one image. The at least one updated image may depict one or more anatomical elements, which may be the same as or similar to the one or more anatomical elements depicted in the at least one image. In some embodiments, the at least one updated image may be obtained from at least one of the one or more poses. In other embodiments, the at least one updated image may be obtained from one or more updated poses.

The at least one updated image may be obtained automatically. For example, the imaging device may continuously obtain images subsequent to the at least one image. In another example, the imaging device may obtain images at a time interval. In other embodiments, the at least one updated image may be obtained when a user such as a surgeon or other medical provider inputs instructions for the imaging device to obtain the at least one updated image. In such embodiments, the user may, for example, wish to confirm a pose of an anatomical element, or may be aware of a shift or change to an anatomical element and may wish to update the three-dimensional representation with such new information.

The method 600 also comprises comparing the at least one image to the at least one updated image (step 608). The at least one image may be obtained in at step 504 of method 500. In embodiments where a pose, position, orientation, size, or shape of an anatomical element is to be confirmed, the at least one updated image may be compared to corresponding image(s) of the at least one image. Comparing the at least one updated image and the corresponding image(s) of the at least one image may comprise aligning the at least one updated image and the corresponding image(s) of the at least one image and detecting any changes between the images. In such embodiments, the at least one updated image and the corresponding image(s) of the at least one image may be obtained from the imaging device at the same pose. In other embodiments, at least one updated image and the corresponding image(s) of the at least one image may be obtained from different poses. In such embodiments, the one or more anatomical elements depicted in the at least one update image may be aligned with the one or more anatomical elements depicted in corresponding image(s) of the at least one image and changes may be detected between one or more anatomical elements depicted in the images.

The method 600 also comprises registering the at least one updated image to yield at least one updated registered image (step 612). The step 612 may be the same as or similar to the step 508 of method 500 described above.

The method 600 also comprises replacing the at least one registered image with the at least one updated registered image (step 616). The at least one registered image may be replaced by the at least one updated registered image within a display such as the display 126. In some embodiments, the at least one registered image may be replaced with the at least one updated registered image when a change between the at least one registered image and the at least one updated registered image is detected (such as in, for example, step 608). In other embodiments, the at least one registered image may be replaced with the at least one updated registered image regardless of whether a change is detected. In still other embodiments, when a change is not detected, the at least one registered image may not be replaced with the at least one updated registered image. In such embodiments, the at least one updated registered image may be saved to, for example, a memory such as the memory 106, or discarded.

It will be appreciated that in some embodiments, the method does not include step 608. In other words, the step 616 may occur automatically without comparing the at least one registered image with the at least one updated registered image. It will also be appreciated that the steps 612 and/or 616 may not occur if the at least one registered image and the at least one updated registered image are substantially the same or if any changes detected do not reach a threshold.

It will be appreciated that in some embodiments, the steps 604, 608, 612, and/or 616, may be continuously repeated to provide real-time updates regarding a pose, size, shape, position, or orientation of the one or more anatomical elements within the display. In other words, at least one updated image may be obtained continuously, and in some instances, the subsequent updated image may be registered to the patient and displayed on the display. In other instances, a subsequent intraoperative image may be compared to a prior intraoperative image, and if a change is detected, the subsequent intraoperative image may be registered to the patient and displayed in the display. It will also be appreciated that in some embodiments, an intraoperative image may be obtained at a time interval.

The present disclosure encompasses embodiments of the method 600 that comprise more or fewer steps than those described above, and/or one or more steps that are different than the steps described above.

Figure 7:
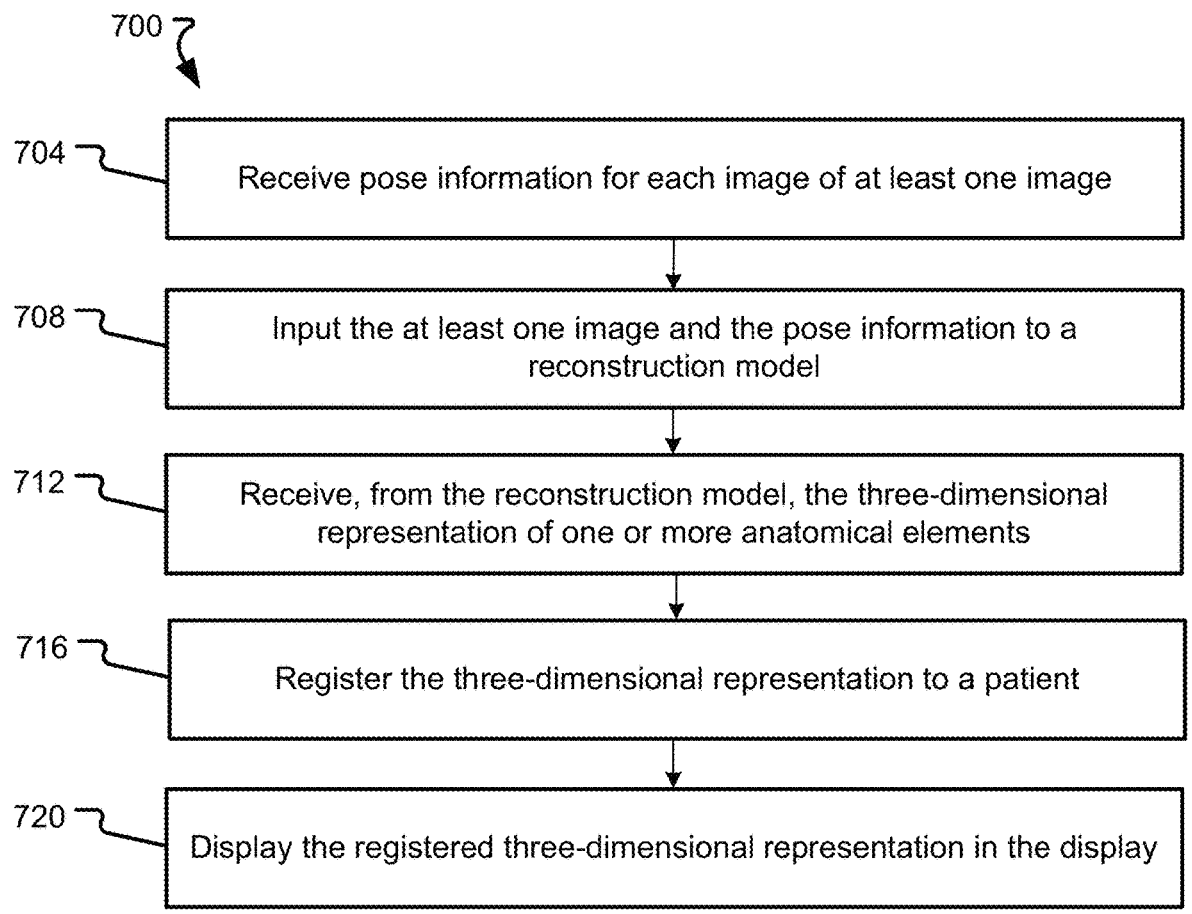
FIG. 7 is a flowchart according to at least one embodiment of the present disclosure.

FIG. 7 depicts a method 700 that may be used, for example, for generating a three-dimensional representation. The method 700 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 700. The at least one processor may perform the method 700 by executing instructions stored in a memory such as the memory 106. The instructions may correspond to one or more steps of the method 700 described below. The instructions may cause the processor to execute one or more algorithms, such as the algorithm 120.

The method 700 comprises receiving pose information for each image of the at least one image (step 704). The pose information may be pose information for each pose of the one or more poses (which correspond to each image of the set of images). As previously described, the pose refers to a position and an orientation. The pose information may be, for example, coordinates of the imaging device when a corresponding image is obtained. In some embodiments, the pose information may be obtained from a navigation system such as the navigation system 118. In such embodiments, the imaging device may include a reference marker or an electromagnetic tracker tracked by the navigation system. In other embodiments, the pose information may be obtained from a robotic arm such as the robotic arm 116 when the imaging device is oriented by the robotic arm. In such embodiments, the robotic arm may comprise a sensor such as the sensor 132 configured to provide pose data of the robotic arm. The sensor may provide pose data of an end of the robotic arm (e.g., a pose of the imaging device disposed at the end of the robotic arm) or may provide pose data of any portion of the robotic arm. In the latter instances, a pose of the imaging device can be determined from the pose data based on a distance between the portion of the robotic arm and the imaging device.

It will be appreciated that in some embodiments, the pose information may only contain information about a position or an orientation of the imaging device.

The method 700 also comprises inputting the at least one image and pose information to a reconstruction model (step 708). The reconstruction model may be the same as or similar to the reconstruction model 206, 124. The reconstruction model may be configured to generate a three-dimensional representation of the one or more anatomical elements based on the set of images and the pose information. In some embodiments, the preoperative image and corresponding preoperative pose information may also be inputted into the reconstruction model. In some embodiments, the reconstruction model may generate the three-dimensional representation of the one or more anatomical elements based on the set of images, the pose information, the preoperative image, and the preoperative pose information. In other instances, the reconstruction model may output a separate three-dimensional representation of one or more anatomical elements depicted in the preoperative image. In such instances, the three-dimensional representation of the one or more anatomical elements depicted in the set of images may be overlaid or combined with the three-dimensional representation of the one or more anatomical elements depicted in the preoperative image. For example, the three-dimensional representation of the one or more anatomical elements depicted in the set of images may be formed from ultrasound images, which may be overlaid onto the three-dimensional representation of the one or more anatomical elements depicted in the preoperative image, which may be formed from X-ray images. Thus, in such examples, soft tissue information (as obtained from the ultrasound images) and hard tissue information (as obtained from the X-ray images) may both be provided for the one or more anatomical elements.

The reconstruction model may be trained using historical sets of image(s) and/or historical pose information. In some embodiments, the historical sets of image(s) may depict one or more anatomical elements similar to the one or more anatomical elements depicted by the preoperative image and/or the set of images. In other embodiments, the historical sets of image(s) may depict one or more anatomical elements different from the one or more anatomical elements depicted by the preoperative image and/or the set of images.

Generating the three-dimensional representation may include determining a surface representation or virtual boundary of the one or more anatomical elements depicted in the set of images (and, in some cases, the preoperative image) based on the corresponding pose information (and, in some cases, the preoperative pose information). More specifically, in some embodiments, each image may be positioned adjacent to another image based on the respective corresponding pose information and a surface representation may be formed based the relative position of surfaces depicted in each image.

The method 700 also comprises receiving, from the reconstruction model, the three-dimensional representation (step 712). As previously described, the three-dimensional representation of the one or more anatomical elements may comprise a surface representation of the one or more anatomical elements. In some embodiments, the surface representation may be a virtual mesh. The three-dimensional representation may also comprise pose information of the one or more anatomical elements. In some embodiments, the three-dimensional representation may comprise hard tissue and/or soft tissue information. Further, the three-dimensional representation may be measured to provide information about a size, volume, dimensions, or shape of the one or more anatomical elements.

The method 700 also comprises registering the three-dimensional representation to a patient (step 716). The step 716 may be the same as or similar to the step 508 of method 500 described above.

The method 700 also comprises displaying the registered three-dimensional representation in the display (step 720). The step 720 may be the same as or similar to the step 512 of method 500 described above. It will be appreciated that the three-dimensional representation may be overlaid onto a corresponding anatomical element. In other words, the three-dimensional representation of an anatomical element may be overlaid onto the physical anatomical element. In other instances, the three-dimensional representation may be displayed on a fixed portion of the display.

The three-dimensional representation may be similarly updated (whether incrementally or in real-time) using the method 600 described above.

The present disclosure encompasses embodiments of the method 700 that comprise more or fewer steps than those described above, and/or one or more steps that are different than the steps described above.

It will be appreciated that any of the steps of methods 400, 500, 600 and/or 700 may be combined in any order. For example, some steps of method 400 and some steps of method 600 may be combined and executed. As noted above, the present disclosure encompasses methods with fewer than all of the steps identified in FIGS. 4-7 (and the corresponding description of the methods 400, 500, 600, 700), as well as methods that include additional steps beyond those identified in FIGS. 4-7 (and the corresponding description of the methods 400, 500, 600, 700). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system comprising:
   an image device comprising an ultrasound image device;
   a display configured to display at least one image over an environment;
   a processor; and
   a memory storing data for processing by the processor, the data, when processed, causing the processor to:
      receive the at least one image from the ultrasound image device, the at least one image received from the ultrasound image device comprising at least one ultrasound image;
      receive information about a field of view in the environment;
      identify, by the processor using feature recognition, one or more objects in the field of view;
      register the at least one ultrasound image to a patient to yield at least one registered ultrasound image;
      display the at least one registered ultrasound image in the display based on the one or more objects identified in the field of view, the display displaying the at least one registered ultrasound image over the environment;
      receive at least one updated ultrasound image from the ultrasound image device; compare the at least one ultrasound image to the at least one updated ultrasound image;
      register the at least one updated ultrasound image to the patient to yield at least one updated registered ultrasound image when a difference between the at least one ultrasound image and the at least one updated ultrasound image is detected; and replace the at least one registered ultrasound image with the at least one updated registered ultrasound image in the display, wherein the at least one ultrasound image comprises a plurality of ultrasound images, wherein the registered ultrasound image comprises a three-dimensional ultrasound image, and wherein the data, when processed, causes the processor to generate the three-dimensional ultrasound image from the plurality of ultrasound images by:

receiving pose information of the ultrasound image device for each ultrasound image of the plurality of ultrasound images, the pose information comprising a position and orientation of the ultrasound image device when a respective ultrasound image was captured;

positioning each of the plurality of ultrasound images adjacent to another one of the plurality of ultrasound images based on the pose information for each ultrasound image; and forming a surface representation of one or more anatomical elements in the plurality of ultrasound images based on relative positions of surfaces of the one or more anatomical elements depicted in the positioned ultrasound images.

2. The system of claim 1, further comprising a navigation system configured to use the at least one registered ultrasound image for navigation of at least one surgical instrument, wherein the memory stores further data for processing by the processor that, when processed, causes the processor to:

generate instructions for navigating the at least one surgical instrument based on the at least one registered ultrasound image.

3. The system of claim 1, wherein the display comprises a headset display.

4. The system of claim 1, wherein the at least one ultrasound image is displayed semi-transparently with respect to the environment.

5. The system of claim 1, wherein the at least one ultrasound image is overlaid opaquely over the environment.

6. The system of claim 1, wherein displaying the at least one registered ultrasound image displays the at least one registered ultrasound image in a doppler mode.

7. The system of claim 1, wherein displaying the at least one registered ultrasound image displays the at least one registered ultrasound image in real-time.

8. The system of claim 1, wherein the memory stores further data for processing by the processor that, when processed, causes the processor to:

receive information about the environment visible in the display, the information comprising a position and an orientation of the patient; and display one or more of the at least one registered ultrasound image correlating to the position and orientation of the patient.

9. A device comprising:
a processor; and
a memory storing data for processing by the processor, the data, when processed, causing the processor to:
receive at least one ultrasound image from an ultrasound image device;
register the at least one ultrasound image to a patient to yield a at least one registered ultrasound image;

receive information about a field of view in an environment;

identify, by the processor using feature recognition, one or more objects in the field of view;

display the at least one registered ultrasound image on a display based on the one or more objects identified in the field of view;

receive at least one updated ultrasound image from the ultrasound image device;

compare the at least one ultrasound image to the at least one updated ultrasound image;

register the at least one updated ultrasound image to the patient to yield at least one updated registered ultrasound image when a difference between the at least one ultrasound image and the at least one updated ultrasound image is detected; and replace the at least one registered ultrasound image with the at least one updated registered ultrasound image in the display, wherein the at least one ultrasound image comprises a plurality of ultrasound images, wherein the registered ultrasound image comprises a three-dimensional ultrasound image, and wherein the data, when processed, causes the processor to generate the three-dimensional ultrasound image from the plurality of ultrasound images by:

receiving pose information of the ultrasound image device for each ultrasound image of the plurality of ultrasound images, the pose information comprising a position and orientation of the ultrasound image device when a respective ultrasound image was captured;

positioning each of the plurality of ultrasound images adjacent to another one of the plurality of ultrasound images based on the pose information for each ultrasound image; and forming a surface representation of one or more anatomical elements in the plurality of ultrasound images based on relative positions of surfaces of the one or more anatomical elements depicted in the positioned ultrasound images.

10. The device of claim 9, further comprising a navigation system configured to use the at least one registered ultrasound image for navigation of at least one surgical instrument, wherein the memory stores further data for processing by the processor that, when processed, causes the processor to:

generate instructions for navigating the at least one surgical instrument based on the at least one registered ultrasound image.

11. The device of claim 9, wherein the at least one ultrasound image is displayed semi-transparently with respect to an environment.

12. A system comprising:
an image device comprising an ultrasound image device;
a navigation system;
a display configured to display one or more images overlaid over an environment;
a processor; and
a memory storing data for processing by the processor, the data, when processed, causing the processor to:
receive one or more images from the ultrasound image device, the one or more images received from the ultrasound image device comprising one or more ultrasound images;
register the one or more ultrasound images to a patient to yield one or more registered ultrasound images;

receive information about a field of view in the environment;
identify, by the processor using feature recognition, one or more objects in the field of view;
display the one or more registered ultrasound images over an environment in the display based on the one or more objects identified in the field of view;
generate instructions for navigating at least one surgical instrument based on the one or more registered ultrasound images;
receive at least one updated ultrasound image from the ultrasound image device;
compare the one or more ultrasound images to the at least one updated ultrasound image;
register the at least one updated ultrasound image to the patient to yield at least one updated registered ultrasound image when a difference between the one or more ultrasound images and the at least one updated ultrasound image is detected; and
replace the one or more registered ultrasound images with the at least one updated registered ultrasound image in the display, wherein the one or more ultrasound images comprise a plurality of ultrasound images, wherein the one or more registered ultrasound images comprise a three-dimensional ultrasound image, and wherein the data, when processed, causes the processor to generate the three-dimensional ultrasound image from the plurality of ultrasound images by:
receiving pose information of the ultrasound image device for each ultrasound image of the plurality of ultrasound images, the pose information comprising a position and orientation of the ultrasound image device when a respective ultrasound image was captured;
positioning each of the plurality of ultrasound images adjacent to another one of the plurality of ultrasound images based on the pose information for each ultrasound image; and
forming a surface representation of one or more anatomical elements in the plurality of ultrasound images based on relative positions of surfaces of the one or more anatomical elements depicted in the positioned ultrasound images.

* * * * *